(12) United States Patent
Percec et al.

(10) Patent No.: US 8,614,347 B2
(45) Date of Patent: Dec. 24, 2013

(54) FLUOROUS DENDRIMERS AND METHODS FOR PRODUCTION THEREOF

(75) Inventors: Virgil Percec, Philadelphia, PA (US); Christopher J. Wilson, Rotherham (GB); Daniela A. Wilson, Rotherham (GB); Andrew E Feiring, Wilmington, DE (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 76 days.

(21) Appl. No.: 13/456,607

(22) Filed: Apr. 26, 2012

(65) Prior Publication Data

US 2012/0277460 A1  Nov. 1, 2012

Related U.S. Application Data

(60) Provisional application No. 61/479,188, filed on Apr. 26, 2011.

(51) Int. Cl.
C07C 69/76 (2006.01)

(52) U.S. Cl.
USPC .............................................. 560/61; 500/62

(58) Field of Classification Search
None
See application file for complete search history.

(56) References Cited

U.S. PATENT DOCUMENTS

2011/0218353 A1* 9/2011 Drysdale et al. ................ 560/60

OTHER PUBLICATIONS

Database CAPLUS Chemical Abstracts Service, Columbus, Ohio, US; Database Accession No. 1992:73028, Abstract of Drysdale et al., WO 2011028767, Mar. 10, 2011.*
Wilson et al., Journal of Polymer Science, Part A: Polymer Chemistry (2010), 48(11), 2498-2508.*
Attached Wiley Online Library Abstract of Wilson et al., Journal of Polymer Science, Part A: Polymer Chemistry (2010), 48(11), 2498-2508, Copyright © 2010 Wiley Periodicals, Inc.*
Balagurusamy et al., "Rational Design of the First Spherical Supramolecular Dendrimers Self-Organized in a Novel Thermotropic Cubic Liquid-Crystalline Phase and the Determination of Their Shape by X-ray Analysis," J. Am. Chem. Soc., Feb. 19, 1997, 119(7), 1539-1555.
Barthel-Rosa et al., "Chemistry in fluorous media: a user's guide to practical considerations in the application of fluorous catalysts and reagents," Coord. Chem. Rev., Sep. 1999, 192, 587-605.
Bilgiçer et al., "Synthesis and thermodynamic characterization of self-sorting coiled coils," Tetrahedron, May 13, 2002, 58(20), 4105-4112.
Bozdemir et al., "Convergent Synthesis of Fluorinated Dendrons Using the Mesylate Activation Route," Turk. J. Chem., Aug. 2007, 31(3), 389-396.
Caminade et al., "Fluorinated dendrimers," Curr. Opin. Colloid Interface, Aug. 2003, 8(3), 282-295.
Chiu et al., "Helix Propensity of Highly Fluorinated Amino Acids," J. Am. Chem. Soc., Dec. 13, 2006, 128(49), 15556-15557.
Chvalun et al., "Structure of gyroid mesophase formed by monodendrons with fluorinated alkyl tails," Polym. Sci. Series A, Feb. 2007, 49(2), 158-167.
Chvalun et al., "Two- and three-dimensional mesophases formed by monodendrons based on gallic acid with partially fluorinated alkyl tails," Polym. Sci. Series A, 2002, 44(12), 1281-1289.

(Continued)

*Primary Examiner* — Karl J Puttlitz
(74) *Attorney, Agent, or Firm* — Woodcock Washburn, LLP

(57) ABSTRACT

The present invention concerns the design of an environmentally friendly and efficient fluorous phase based on dendritic architectures containing short semifluorinated groups on their periphery.

17 Claims, 4 Drawing Sheets

(56) References Cited

OTHER PUBLICATIONS

Farnham, W. B., "Fluorinated Carbanions," Chem. Rev., Aug. 1, 1996, 96(5), 1633-1640.
Fast et al., "Fluoropolymer-based Emulsions for the Intravenous Delivery of Sevoflurane," Anesthesiology, Oct. 2008, 109(4), 651-656.
Guo et al., "Alternative Fluoropolymers to Avoid the Challenges Associated with Perfluorooctanoic Acid," Ind. Eng. Chem. Res., Feb. 6, 2008, 47(3), 502-508.
Iha et al., "Applications of Orthogonal "Click" Chemistries in the Synthesis of Functional Soft Materials," J. Chem. Rev., Nov. 11, 2009, 109(11), 5620-5686.
Jaipuri et al., "Synthesis and Quantitative Evaluation of Glycero-D-manno-heptose Binding to Concanavalin A by Fluorous-Tag Assistance," Angew Chem., Feb. 15, 2008, 120(9), 1731-1734.
Ko et al., "Fluorous-Based Carbohydrate Microarrays," J. Am. Chem. Soc., Sep. 28, 2005, 127(38), 13162-13163.
Krafft et al., "Emulsions and microemulsions with a fluorocarbon phase," Curr. Opin. Colloid Interface, Aug. 2003, 8(3), 251-258.
Krafft et al., "Perfluorocarbons: Life sciences and biomedical uses Dedicated to the memory of Professor Guy Ourisson, a true Renaissance man," J. Polym. Sci. Part A, Apr. 1, 2007, 45(7), 1185-1198.
Lee et al., "Acid-Sensitive Semiperfluoroalkyl Resorcinarene: An Imaging Material for Organic Electronics," J. Am. Chem. Soc., Sep. 3, 2008, 130(35), 11564-11565.
Luscombe et al., "Synthesis of Supercritical Carbon Dioxide Soluble Perfluorinated Dendrons for Surface Modification," J. Org. Chem., Jul. 20, 2007, 72(15), 5505-5513.
Martin-Rapún et al., "Liquid crystalline semifluorinated ionic dendrimers," Liquid Crystals, Mar. 2007, 34(3), 395-400.
Percec et al., "Cell membrane as a model for the design of semifluorinated ion-selective nanostructured supramolecular systems," Tetrahedron, May 13, 2002, 58(20), 4031-4040.
Percec et al., "Designing Libraries of First Generation AB3 and AB2 Self-Assembling Dendrons via the Primary Structure Generated from Combinations of (AB)y-AB3 and (AB)y-AB2 Building Blocks," J. Am. Chem. Soc., May 19, 2004, 126(19), 6078-6094.
Percec et al., "Expanding the Structural Diversity of Self-Assembling Dendrons and Supramolecular Dendrimers via Complex Building Blocks," J. Am. Chem. Soc., Sep. 12, 2007, 129(36), 11265-11278.
Percec et al., "Exploring and Expanding the Structural Diversity of Self-Assembling Dendrons through Combinations of AB, Constitutional Isomeric AB2, and AB3 Biphenyl-4-Methyl Ether Building Blocks," Chem. Eur. J., Aug. 16, 2006, 12(24), 6216-6241.
Percec et al., "Molecular engineering of side-chain liquid-crystalline polymers by living cationic polymerization," Adv. Mat., Sep. 1992, 4(9), 548-561.
Percec et al., "Semifluorinated polymers: 1. Synthesis and characterization of side chain liquid crystalline polymers containing semifluorinated oligooxyethylene based flexible spacers," Polymer, 1991, 32(10), 1897-1908.
Percec et al., "Synthesis and Retrostructural Analysis of Libraries of AB3 and Constitutional Isomeric AB2 Phenylpropyl Ether-Based Supramolecular Dendrimers," J. Am. Chem. Soc., Mar. 15, 2006, 128(10), 3324-3334.
Percec et al., "Synthesis and Structural Analysis of Two Constitutional Isomeric Libraries of AB2-Based Monodendrons and Supramolecular Dendrimers," J. Am. Chem. Soc., Feb. 21, 2001, 123(7), 1302-1315.
Percec et al., "Synthesis of aromatic polyethers by Scholl reaction. II. On the polymerizability of 4,4'-bis(phenoxy)diphenyl sulfones and of 4,4'-bis(phenythiol)diphenyl sulfone," J. Polym. Sci. Part A, Jun. 1991, 29(7), 949-964.
Percec, V., "Bioinspired supramolecular liquid crystals," Phil. Trans. R. Soc. A, Oct. 15, 2006, 364(1847), 2709-2719.
Pitois et al., "Fluorinated dendritic polymers and dendrimers for waveguide applications," Optical Materials, Jan. 2003, 21(1-3), 499-506.
Pitois et al., "Functionalized Fluorinated Hyperbranched Polymers for Optical Waveguide Applications," Adv. Mat., Oct. 2001, 13(19), 1483-1487.
Pitois et al., "Lanthanide-cored fluorinated dendrimer complexes: synthesis and luminescence characterization," J. Luminescence, Mar. 2005, 111(4), 265-283.
Rosen et al., "Predicting the Structure of Supramolecular Dendrimers via the Analysis of Libraries of AB3 and Constitutional Isomeric AB2 Biphenylpropyl Ether Self-Assembling Dendrons," J. Am. Chem. Soc., Dec. 2, 2009, 131(47), 17500-17521.
Rosen et al., "Synthesis of dendrimers through divergent iterative thio-bromo "Click" chemistry," J. Polym. Sci. Part A, Aug. 1, 2009, 47(15), 3931-3939.
Rosen et al., "Synthesis of dendritic macromolecules through divergent iterative thio-bromo "Click" chemistry and SET-LRP," J. Polym. Sci. Part A, Aug. 1, 2009, 47(15), 3940-3948.
Studer et al., "Fluorous Synthesis: A Fluorous-Phase Strategy for Improving Separation Efficiency in Organic Synthesis," Science, Feb. 7, 1997, 275(5301), 823-826.
Tang et al., "Biosynthesis of a Highly Stable Coiled-Coil Protein Containing Hexafluoroleucine in an Engineered Bacterial Host," J. Am. Chem. Soc., Nov. 7, 2001, 123(44), 11089-11090.
Tang et al., "Stabilization of Coiled-Coil Peptide Domains by Introduction of Trifluoroleucine," Biochemistry, Mar. 6, 2001, 40(9), 2790-2796.
Tomalia, D. A., "Supramolecular chemistry: Fluorine makes a difference," Nature Materials, Nov. 2003, 2(11), 711-712.
Uneyama et al., "α-Trifluoromethylated Carbanion Synthons," Acc. Chem. Res., Jul. 2008, 41(7), 817-829.
Vegas et al., "Fluorous-Based Small-Molecule Microarrays for the Discovery of Histone Deacetylase Inhibitors," Angew Chem. Int. Ed., Oct. 22, 2007, 46(42), 7960-7964.
West et al., "Theoretical studies of the supramolecular synthon benzene hexafluorobenzene," J. Phys. Org. Chem., May 1997, 10(5), 347-350.
Yoshioka et al., "Synthesis and applications of novel fluorinated dendrimer-type copolymers by the use of fluoroalkanoyl peroxide as a key intermediate," J. Colloid Interface Science, Apr. 1, 2007, 308(1), 4-10.
Zhang, W., "Fluorous Synthesis of Heterocyclic Systems," Chem. Rev., May 2004, 104(5), 2531-2556.
Zhang, W., "Green chemistry aspects of fluorous techniques—opportunities and challenges for small-scale organic synthesis," Green Chemistry, May 2009, 11(7), 911-920.
Zhao et al., "Fluorescent Conjugated Dendrimers with Fluorinated Terminal Groups: Nanofiber Formation and Electroluminescence Properties," Organic Letters, Jul. 17, 2008, 10(14), 3041-3044.

* cited by examiner

FLUOROUS DENDRIMERS AND METHODS FOR PRODUCTION THEREOF

CROSS-REFERENCE TO RELATED APPLICATIONS

The present application claims priority to U.S. Application No. 61/479,188, "Disassembly via an Environmentally Friendly and Efficient Fluorous Phase Constructed with Dendritic Architectures," filed on Apr. 26, 2011, which application is incorporated herein by reference in its entirety for any and all purposes.

GOVERNMENT SUPPORT

This work was supported by a grant from the National Science Foundation (DMR-0548559 and DMR-0520020). Pursuant to 35 U.S.C. §202, the government may have certain rights in the invention.

FIELD

The present invention concerns fluorous dendrimers and methods of their production.

BACKGROUND

In the past decade fluorous chemistry emerged as an influential strategy that facilitates new and efficient methodologies for catalysis, protecting groups, tags, separation processes, microarrays, organic electronics, medicine, self-assembly, liquid crystals, mediate the solubility of polymers, and that of proteins and peptoids folding. Many societal conveniences, ranging from nonstick frying pans, to optics, electronics, displays, fuel and solar cells, rechargeable batteries, drugs, and medical applications rely on the same building blocks, namely, various combinations of linear hydrocarbons with perflooctyl or longer perfluorinated fragments that are used currently to generate the fluorous phase. These compounds degrade to the environmentally biopersistent and potentially toxic perfluoro acids (PFOA). The Environmental Protection Agency (EPA) has the goal to reduce emissions and product content of PFOA by 95% no later than 2010, and completely eliminate it by 2015. Thus, there is a pressing challenge to develop new innovative strategies of chemical design and synthesis that will allow the field of fluorous chemistry not only to continue but to expand into new technological frontiers previously prohibited by cost and environmental concerns. The key requirement is to achieve an efficient fluorous effect by molecular design using a minimum amount of expensive fluorine and short perfluoroalkyl groups. Perfluorobutanoic acid and shorter acids do not bioacumulate in the human body and are not persistent. Self-assembling dendrons and dendrimers containing perfluoroalkyl groups on their periphery, and dendrons and dendrimers containing perfluoroalkyl and perfluoroaryl groups on their periphery have been reported. The amplification of the fluorous phase and fluorous or fluorophobic effect via the dendritic architecture have been recognized since 1995. However, to our knowledge no attempts have been made to elaborate an environmentally friendly and efficient fluorous phase by using the amplification effect of the dendritic architecture.

SUMMARY

In some embodiments, the invention concerns methods of producing fluorous dendrons by a process comprising reacting a compound of formula II

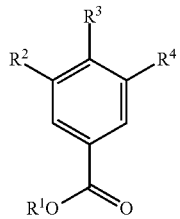

II with a compound of formula III

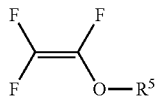

III to produce a compound of the formula I

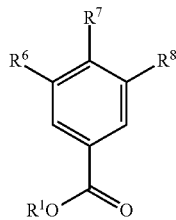

I where $R^1$ is a $C_1$-$C_6$ alkyl group; each of $R^2$-$R^4$ is, independently, H or OH; provided at least two of $R^2$-$R^4$ are OH; $R^5$ is a $C_1$-$C_9$ perfluoroalkyl group, said $C_1$-$C_9$ perfluoroalkyl group optionally containing 1 or 2 ether oxygens; and each of $R^6$-$R^8$ is, independently, H or a group of the formula

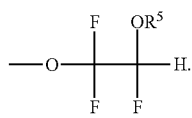

provided that at least two of $R^6$-$R^8$ are a group of the formula

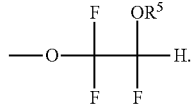

In certain embodiments, $R^1$ is methyl. For some compounds, $R^5$ is a perfluoropropyl group. One preferred perfluoropropyl group is perfluoro-n-propyl.

In another aspect, the invention concerns reacting the compound of formula I with a reducing agent to produce a compound of formula IV.

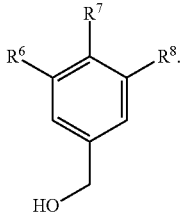

IV

The term "reducing agent" is understood to mean any compound having electron donating properties. In the present invention, such agents are capable of converting an ester group to an alcohol. A wide range of reducing agents is known to those skilled in the art. Some reducing agents are compounds based on boron or aluminum such as the boron or aluminum hydrides such as sodium borohydride ($NaBH_4$) or lithium aluminum hydride ($LiAlH_4$). One preferred reducing agent is $LiAlH_4$.

Another aspect of the invention concerns reacting the compound of formula IV with a chlorinating agent to produce a compound of formula V. One preferred chlorinating agent is $SOCl_2$.

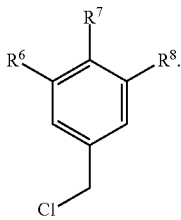

V

In the present invention, a "chlorinating agent" is capable of converting an alcohol to an alkyl chloride. Numerous chlorinating agents are known to those skilled in the art. Such chlorinating agents include, among others, $PCL_3$ and $SOCl_2$. One preferred chlorinating agent is $SOCl_2$.

Yet another aspect of the invention concerns reacting a compound of formula V with a compound of formula

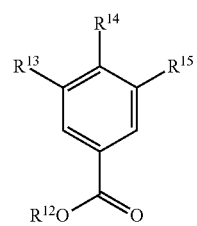

VI to produce a compound of formula VII

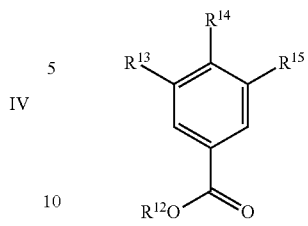

VII where $R^{12}$ is a $C_1$-$C_6$ alkyl group; each of $R^9$, $R^{10}$ and $R^{11}$ is independently H or OH; provided that at least two of $R^9$, $R^{10}$ and $R^{11}$ are OH; each of $R^{13}$, $R^{14}$ and $R^{15}$ is independently H or a group of the formula VIII

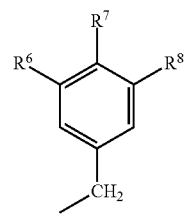

VIII provided that at least two of $R^{13}$, $R^{14}$ and $R^{15}$ are of formula VIII.

The invention also concerns compounds produced by the above methods. One compound is of the formula

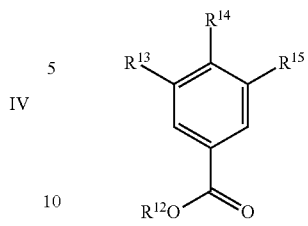

VII where $R^{12}$ is a $C_1$-$C_6$ alkyl group; each of $R^{13}$, $R^{14}$ and $R^{15}$ is independently H or a group of the formula VIII provided that at least two of $R^{13}$, $R^{14}$ and $R^{15}$ are of formula VIII;

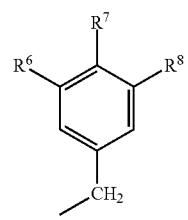

VIII each of $R^6$-$R^8$ is, independently, H or a group of the formula

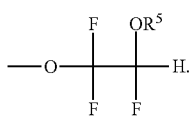

provided that at least two of $R^6$-$R^8$ are a group of the formula

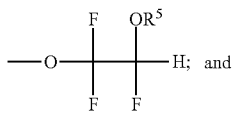

$R^5$ is a $C_1$-$C_9$ perfluoroalkyl group, said $C_1$-$C_9$ perfluoroalkyl group optionally containing 1 or 2 ether oxygens;

In some embodiments, $R^1$ is methyl. Some dendrons have $R^3$ a perfluoropropyl group. One preferred perfluoropropyl group is perfluoro-n-propyl.

Another compound of the invention is of the formula

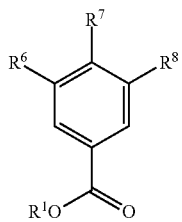

where $R^1$ is a $C_1$-$C_6$ alkyl group; $R^5$ is a $C_1$-$C_9$ perfluoroalkyl group, said $C_1$-$C_9$ perfluoroalkyl group optionally containing 1 or 2 ether oxygens; and each of $R^6$-$R^8$ is, independently, H or a

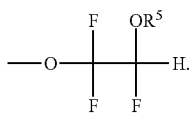

provided that at least two of $R^6$-$R^8$ are a group of the formula

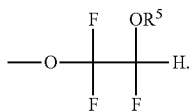

In some embodiments, $R^1$ is methyl. Some dendrons have $R^3$ a perfluoropropyl group. One preferred perfluoropropyl group is perfluoro-n-propyl.

DETAILED DESCRIPTION OF ILLUSTRATIVE EMBODIMENTS

The present invention concerns the design of an environmentally friendly and efficient fluorous phase based on dendritic architectures. This concept can impact many technological applications dominated by environmentally less friendly fluorous phases.

Traditionally the fluorous phase is generated with perfluorinated alkyl groups that are usually perfluorooctyl or longer and are bioaccummulative and biopersistent and therefore, are considered environmentally unfriendly. The present invention concerns a new concept for the construction of the fluorous phase. This concept is based on the amplification of the fluorous effect with the help of dendritic architectures containing very short semifluorinated groups on their periphery. This new concept was demonstrated by the convergent synthesis of the first and second generation AB$_3$ and AB$_2$ benzyl ether dendrons functionalized on their periphery. via catalytic nucleophilic addition of their phenolates to perfluoropropylvinyl ether. The resulting dendrons are liquids. Their fluorous phase affinity was analyzed and demonstrated that the dendritic architecture amplifies the fluorous phase at a specific generation by the number of functional groups on the dendron periphery, and at different generations by increasing their generation number. Therefore, this concept is very efficient for the design and synthesis of new fluorous materials. In addition, by contrast with dendrons containing perfluoroalkyl groups on their periphery, the current dendrons mediate the disassembly of their parent building blocks but do not mediate the self-assembly in a supermolecular architecture.

Figure 1:
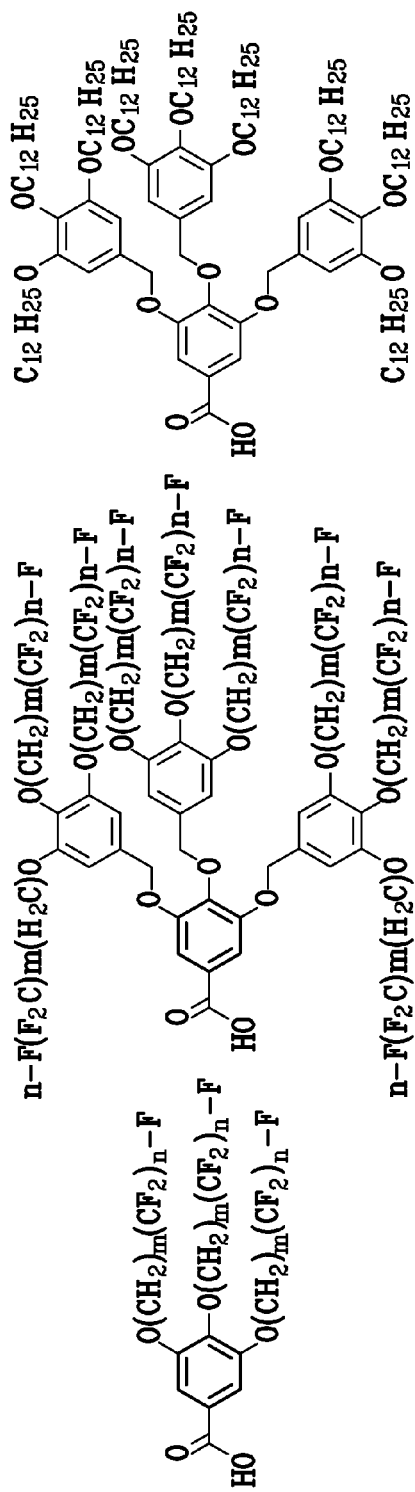
FIG. 1 presents a comparison of the self-assembly of (3,4,5)RfG1-CO$_2$H, (3,4,5)$^2$RfG2-CO$_2$H, and (3,4,5)$^2$12G2-CO$_2$H.
Figure 1:
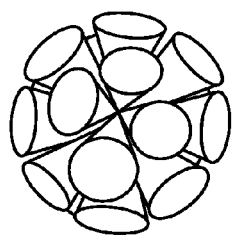
Figure 1:
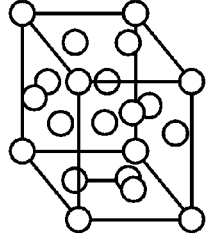
Figure 1:
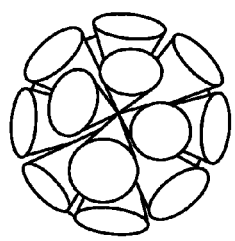
Figure 1:
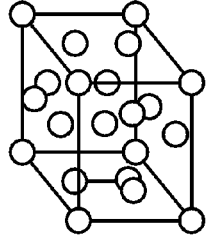
Figure 1:
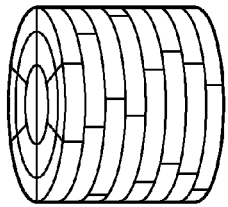
Figure 1:
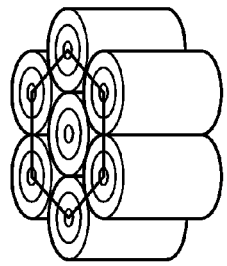

Linear semifluorinated dodecyl groups containing perfluorobutyl, hexyl, and octyl segments on their periphery were discovered in our laboratory to enhance the ability of the first generation AB$_3$ dendrons toward self-assembly and thus mimic, at the first generation, the capabilities encountered only in higher generations of hydrogenated homologous compounds (FIG. 1). The fluorous effect was responsible for this trend.

The corresponding dendronized polymers, and higher generation dendrons, exhibit a decreased solubility in organic solvents even at high temperature while becoming soluble only in fluorinated solvents. Thus, although semifluorinated molecules are known to exhibit enhanced solubility in organic solvents (oleophilicity), semifluorinated dendrons were shown to provide a pathway to oleophobic compounds. This solubility effect is the simplest assay for the fluorous phase and supports the concept of fluorous dendrons. Subsequent results from other laboratories demonstrated the chemical synthesis of oligonucleotides on theses fluorous dendrons. Although these preliminary results were not originally directed toward the solution of the PFOA problem they provide crucial support for the research hypothesis of the experiments to be reported here.

Design and Synthesis of New Fluorous Dendrons

The addition reaction of nucleophiles to fluorinated olefins is an efficient reaction in organofluorine chemistry. Therefore, this can be considered a new "click reaction". The carbanions resulted from this nucleophilic addition can be trapped by a variety of electrophiles. Feiring and Wonchoba reported that the reaction of a phenol with perfluoropropyl vinyl ether (PINE) in DMF in the presence of a catalytic amount of potassium tert-butoxide produced the addition product in 72-96% yield (Scheme 1).

Scheme I. The mechanism of addition of phenol to perfluoropropyl vinyl ether.

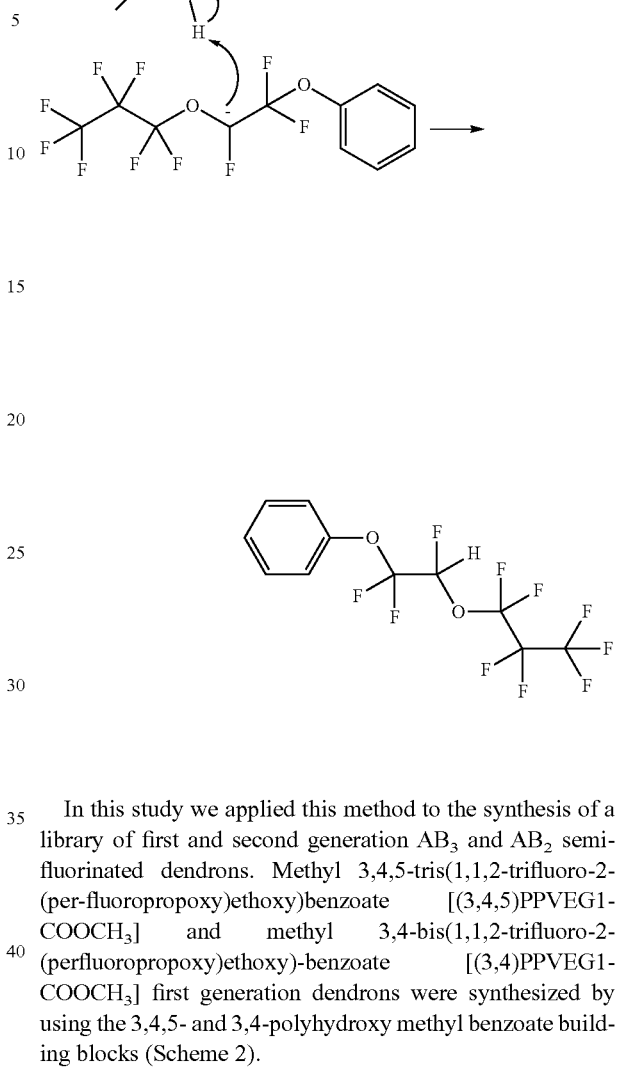

In this study we applied this method to the synthesis of a library of first and second generation AB$_3$ and AB$_2$ semi-fluorinated dendrons. Methyl 3,4,5-tris(1,1,2-trifluoro-2-(per-fluoropropoxy)ethoxy)benzoate [(3,4,5)PPVEG1-COOCH$_3$] and methyl 3,4-bis(1,1,2-trifluoro-2-(perfluoropropoxy)ethoxy)-benzoate [(3,4)PPVEG1-COOCH$_3$] first generation dendrons were synthesized by using the 3,4,5- and 3,4-polyhydroxy methyl benzoate building blocks (Scheme 2).

Scheme 2. Synthesis of first generation dendritic benzyl chlorides (3,4,5)PPVEG1——CH$_2$Cl and (3,4)PPVEG2——CH$_2$Cl.

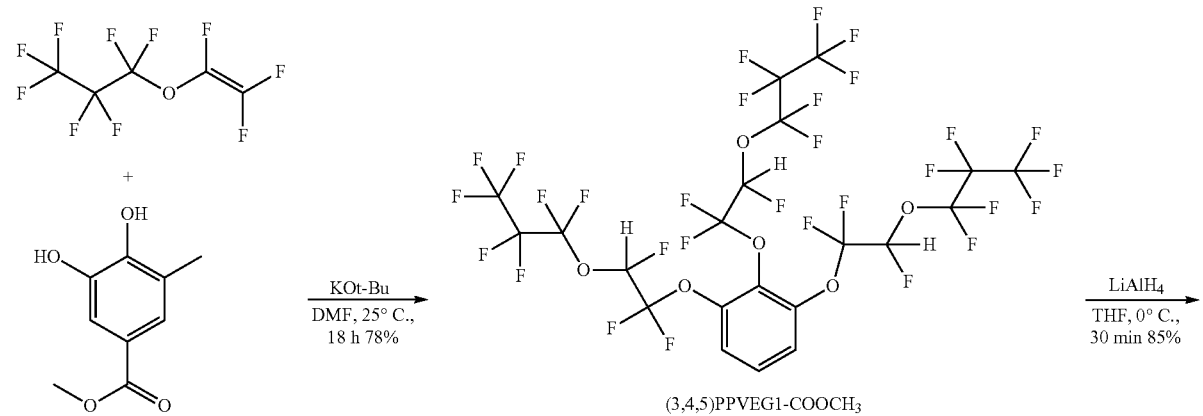

(3,4,5)PPVEG1-COOCH$_3$

-continued
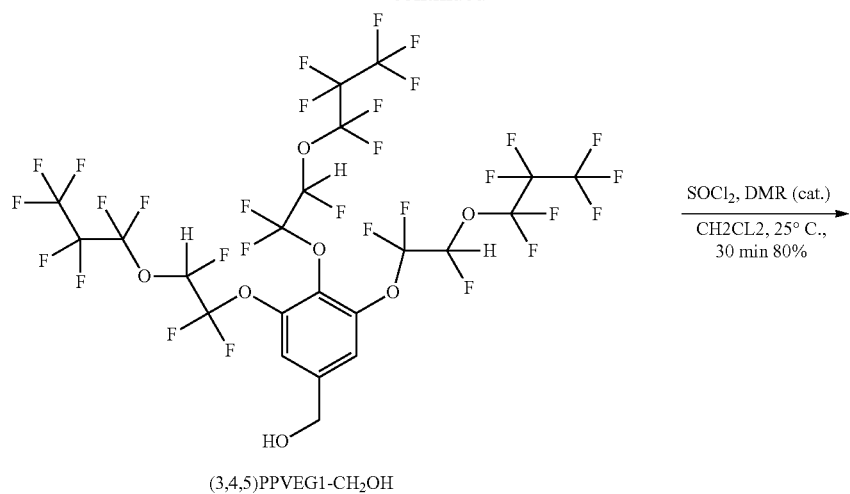
(3,4,5)PPVEG1-CH₂OH
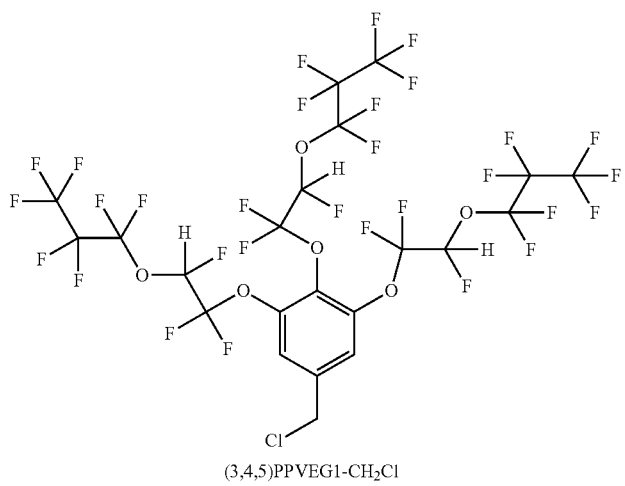
(3,4,5)PPVEG1-CH₂Cl
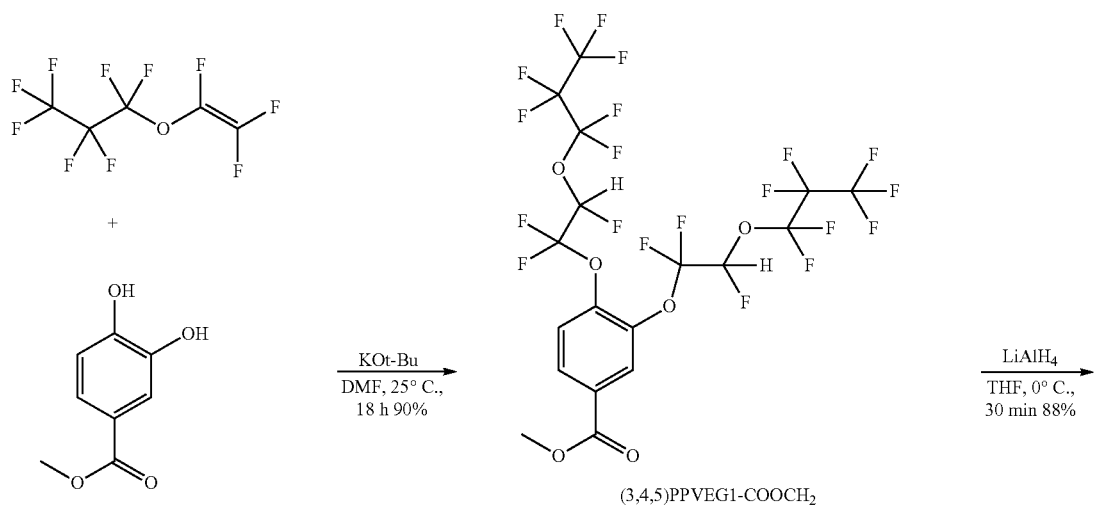
(3,4,5)PPVEG1-COOCH₂

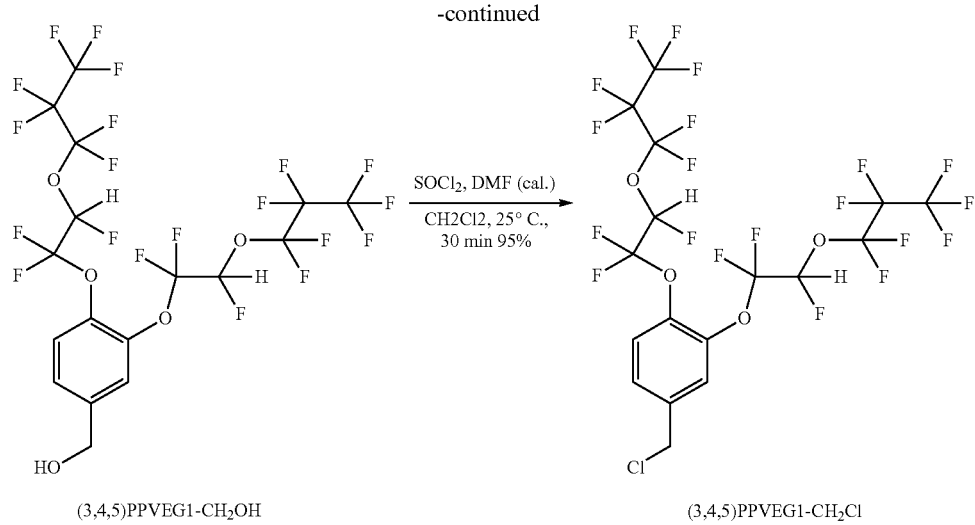

(3,4,5)PPVEG1-CH₂OH → (3,4,5)PPVEG1-CH₂Cl

The short nomenclature for these compounds follows the nomenclature used for the benzyl ether dendrons. We term the PPVE chain to be semifluorinated due to the presence of a single H that results from electrophilic trapping of the carbanion generated from nucleophilic addition of the phenolate to the perfluorinated vinyl ether. Although these chains are closer to perfluorinated chains in structure than to semifluorinated ones the prefix per-should only be applied in cases where all hydrogens are replaced by fluo-rine. In addition to the ease of preparation, the incorporation of an ether bond into the perfluoroalkyl chain fulfills the requirement of higher solubility and eventual degradability to shorter nonbiopersistent molecules. In the case of (3,4,5)PPVEG1-COOCH₃ and (3,4,5)²PPVEG2-COOCH₃, the resulting degradation products are nonpersistent perfluopropyl chains and the naturally occurring gallic acid. Synthesis of the higher generation PPVE dendrons follows a convergent synthesis method previously developed in our laboratory (Schemes 3 and 4). Functionalization of both AB₃ methyl 3,4,5-trihydroxybenzoate and AB₂ methyl 3,4-dihydroxybenzoate was achieved via the nucleophilic addition of the corresponding phenolate to PPVE. This reaction is carried out in anhydrous DMF at 25° C. with a catalytic amount of potassium tert-butoxide. The reaction reaches 100% conversion in 18 h as determined by thin layer chromatography (TLC). The reaction mixture was poured into ice water. Following an acidic workup and purification by column chromatography using neutral alumina and ethylacetate/hexane eluent, a colorless oil was obtained in 70-90% yield. No mono- or di-addition products were recovered from the reaction mixture.

Scheme 3. Synthesis of second generation AB₃ (3,4,5)²PPVEG2-COOCH₃ and AB₂ (3,4)²PPVEG2-COOCH₃ dendrons.

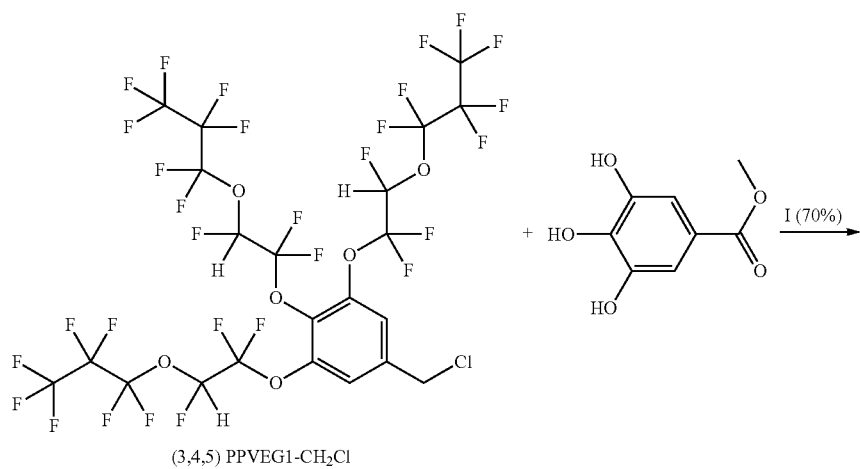

(3,4,5) PPVEG1-CH₂Cl

-continued
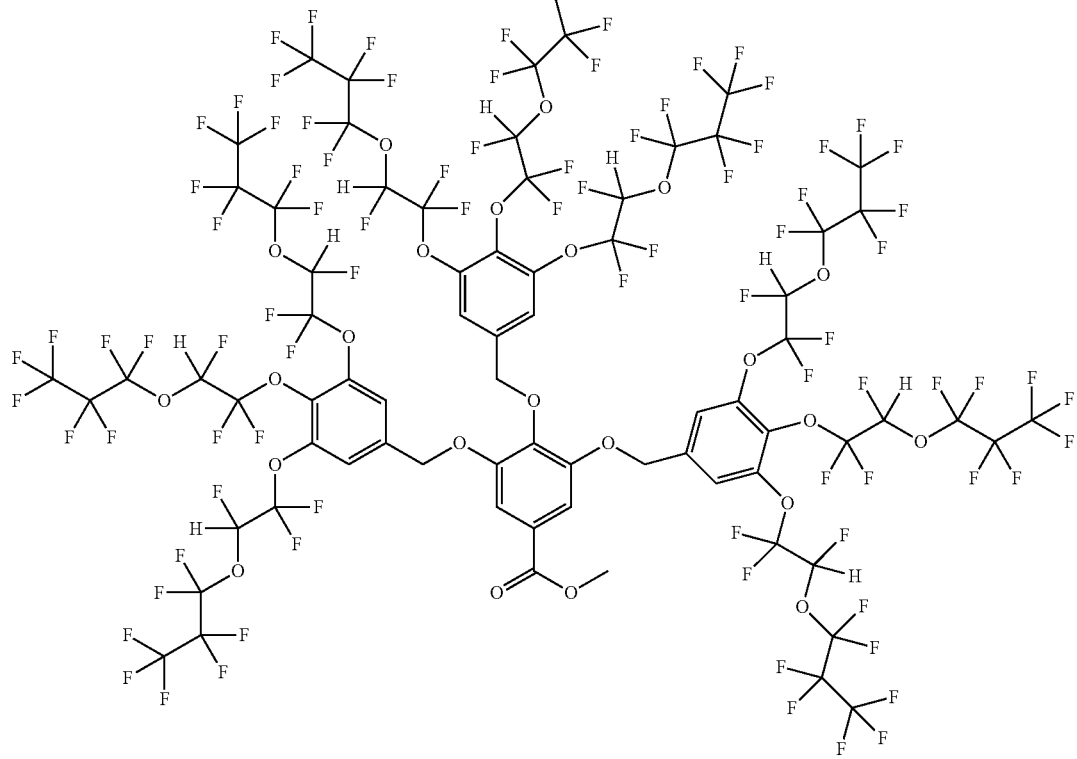
$(3,4,5)^2$PPVEG2-COOCH$_3$
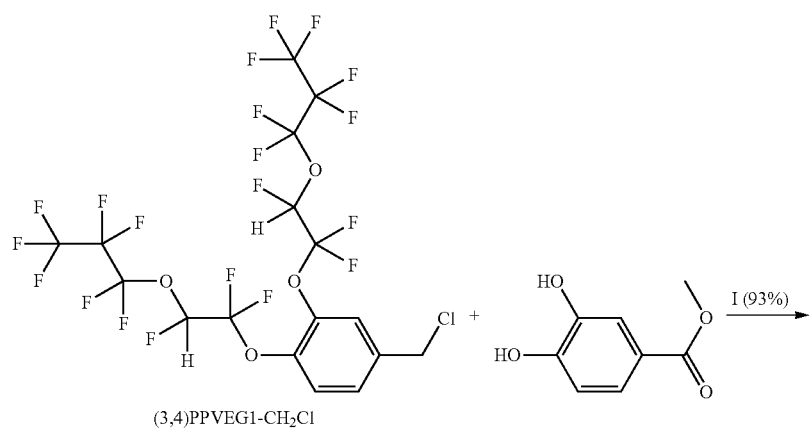

-continued
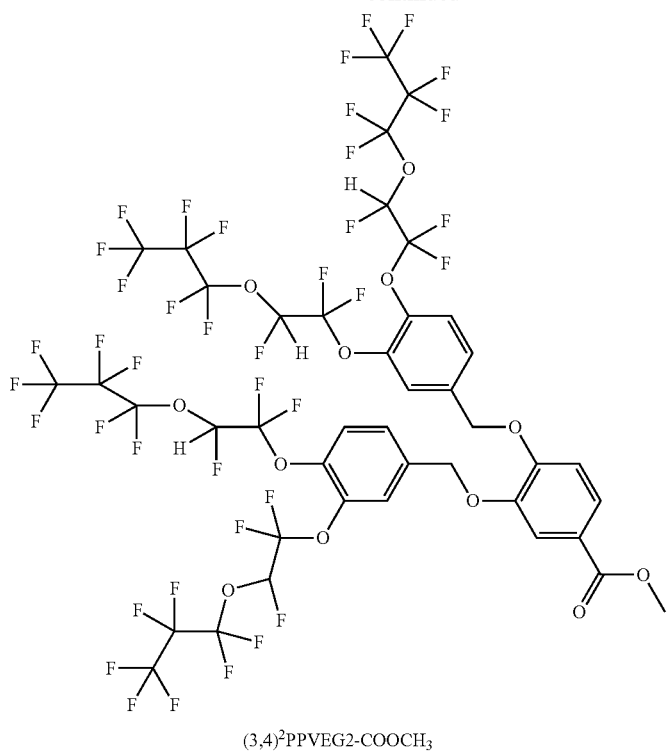
(3,4)²PPVEG2-COOCH₃
i) K₂CO₃, DMF, 65° C., 4-5 h
Scheme 4. Synthesis of constitutional isomeric fluorous dendrons (3,4,5-3,5)PPVEG2-COOCH₃ and (3,4,5-3,4)PPVEG2-COOCH₃.
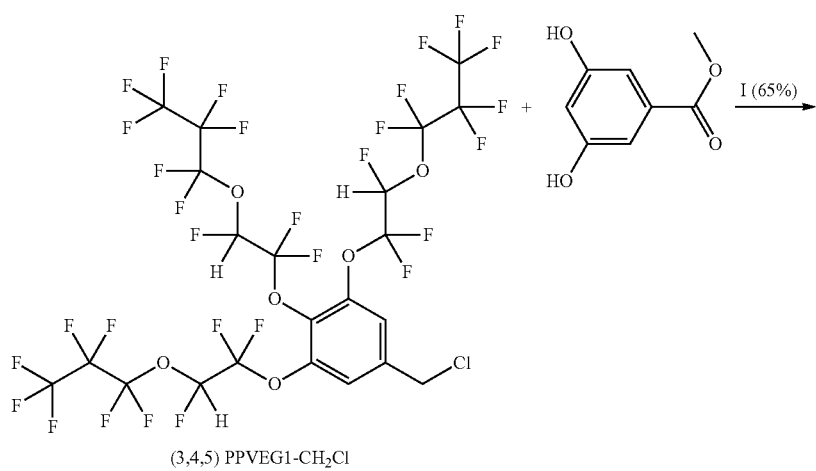
(3,4,5) PPVEG1-CH₂Cl

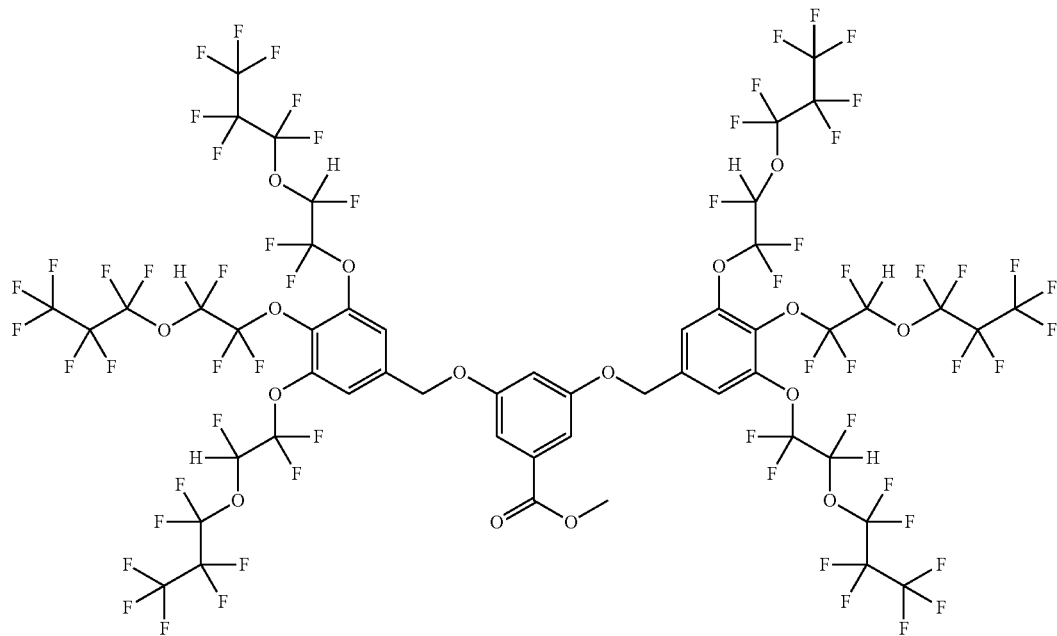
(3,4,5-3,5)PPVEG2-COOCH₃
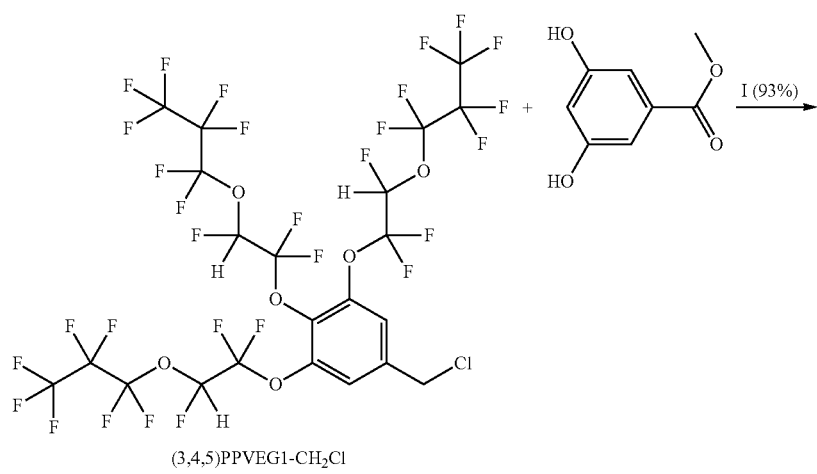
(3,4,5)PPVEG1-CH₂Cl

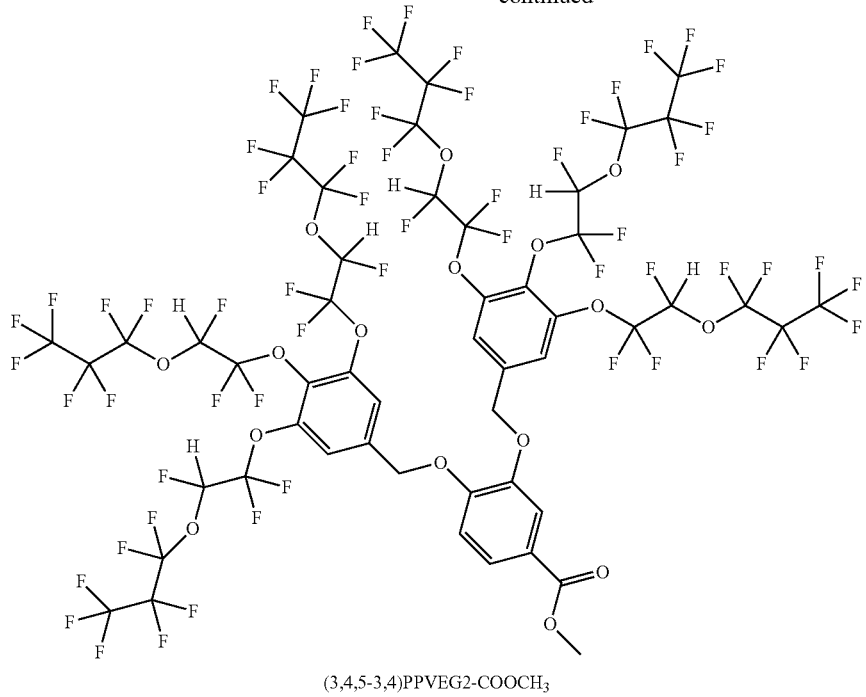

(3,4,5-3,4)PPVEG2-COOCH₃ i) K₂CO₃, DMF, 65° C., 4-5 h

The ester groups of (3,4,5)PPVEG1-COOCH₃ and (3,4) PPVEG1-COOCH₃ wore reduce to the corresponding benzyl alcohols (3,4,5)PPVEG1-CH₂OH and (3,4)PPVEG1-CH₂OH with LiAlH₄ in THF at 0° C. until complete consumption of the starting material was observed by TLC (30 min). After purification on a short plug of silica gel the dendritic benzyl alcohols were obtained as colorless oils in 85-88% yield. The dendritic benzylic alcohols were transformed into dendritic benzyl chlorides (3,4,5)PPVEG1-CH₂Cl and (3,4)PPVEG1CH₂Cl by quantitative chlorination in methylene chloride at 23° C. with SOCl₂ and a catalytic amount of DMF. Consumption of the alcohol was monitored by TLC (30 min). Following an aqueous work up and purification by using a short plug of alumina, a pale yellow oil was obtained in 80-95% yield. This product was used directly in the alkylation step. Our laboratory reported a robust methodology for the quantitative alkyl-ation of dendritic benzyl chlorides with polyhydroxy methyl benzoates in DMF using K₂CO₃ as base that has been efficient in the synthesis of diversity of benzyl ether dendrons. The dendrons (3,4,5) PPVEG1-CH₂Cl and (3,4)PPVEG1-CH₂Cl were alkylated onto methyl 3,4-dihydroxybenzoate, methyl 3,5-dihydroxybenzoate, and methyl 3,4,5-trihydroxybenzoate in DMF using K₂CO₃ at 65° C. The reactions were monitored by TLC until complete consumption of the phenol starting material was observed (4-5 h). This was also indicated by the change in the color of the reaction from the dark brown to an off white indicating complete consumption of the phenolate. The second generation dendrons (3,4,5)²PPVEG2-COOCH₃, (3,4)² PPVEG2-COOCH₃, (3,4,5-3,5)PPVEG2-COOCH₃, and (3,4,5-34)PPVEG2-COOCH₃ were obtained in 65-90% yield after purification by column chromatography.

It was found that the addition of FREON 113 (~3%) to the chromatographic solvent facilitated purification by column chromatography for second generation dendrons.

Figure 2:
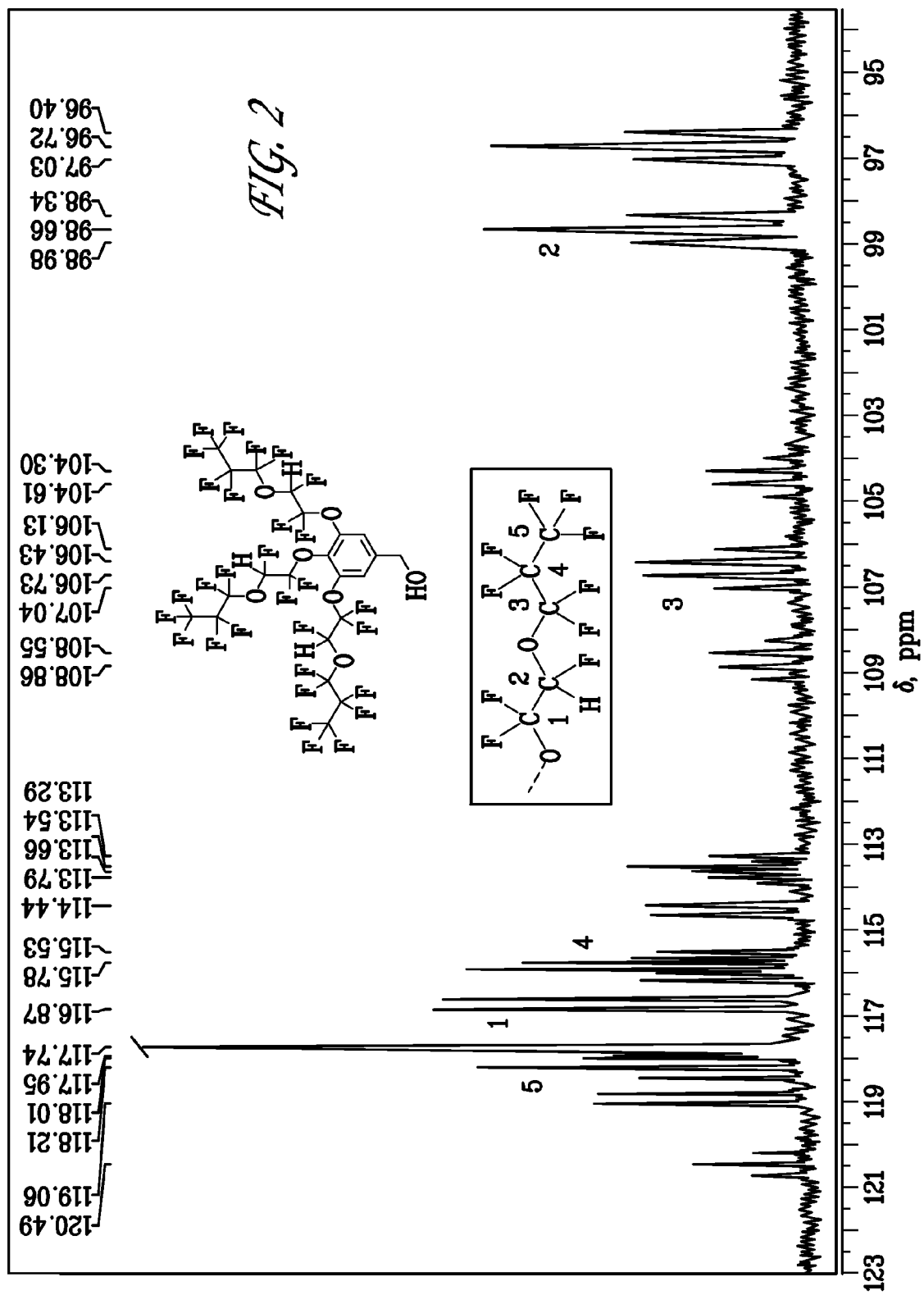
FIG. 2 presents a diagnostic $^{13}$C NMR spectrum showing splitting in (3,4,5)PPVEG1-CH$_2$OH substituted dendron. Expansion of 94-123 ppm region.
Figure 3:
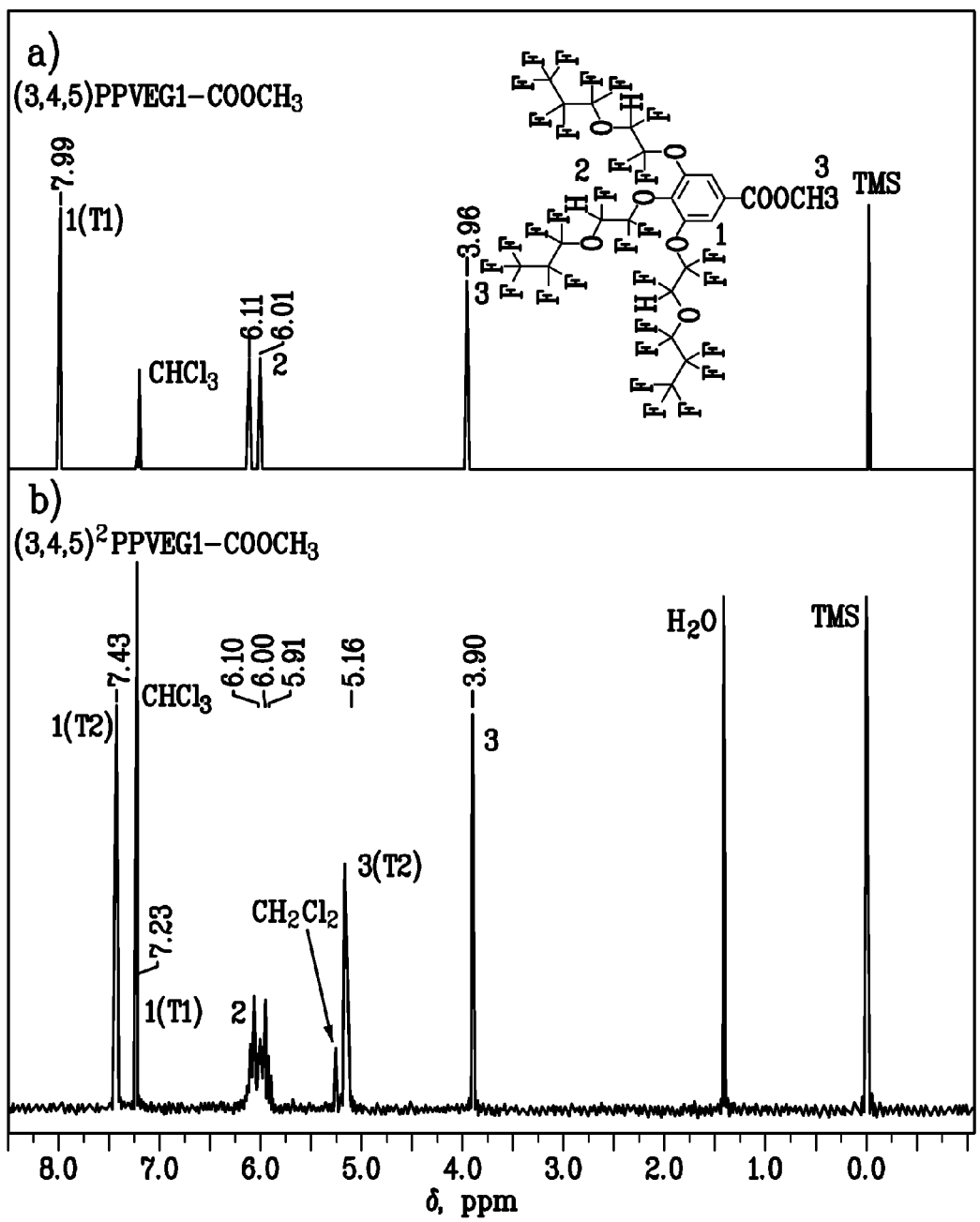
FIG. 3 presents a 500 MHz $^1$H NMR spectra (a) (3,4,5) PPVEG1-CH$_2$OH$_3$ and (b) (3,4,5)$^2$PPVEG1-COOCH$_3$ (CDCl$_3$, TMS, 25° C.).

The PPVE peripheral groups can be identified by their diagnostic $^{13}$C NMR splitting patterns arising from the splitting of the $^{13}$C signal by adjacent $^{19}$F that also has a nuclear spin of ½. Three groups of signals were observed, a doublet of triplets at ~97 ppm, a triplet of quartets at ~106 ppm and a multiplet arising from overlapping of three signals appearing as a triplet of doublets, a triple triplet and a quartet of triplets at ~116 ppm (FIG. 2). The PPVE group can be identified in the $^1$H NMR as a doublet again split by the adjacent spin ½ $^{19}$F at ~6.09 ppm (FIG. 3). As with the previously reported hydrogenated analogues 1-14 NMR analysis of Gener-ation 2 dendrons showed a shift in the central benzene unit aromatic proton signals defined as tier 1 to higher field with increasing generation number. In the case of (3,4,5)²PPVEG2-COOCH₃ a shielding of the aromatic protons in the central benzene unit is observed in comparison to the first generation (3,4,5) PPVEG1COOCH₃ dendron as a 0.76 ppm upfield shift (FIG. 3), Calculation of the Partition Coefficients of Fluorinated Dendrons by Gravimetric Method Partition coefficients of fluorinated compounds represent the Equilibrium distribution of the fluorous compound between two immiscible phases. It was expected that 3,4,5-trisubstituted fluorinated dendrons would create a high concentration of fluorous component and an increased partition coefficient into the fluorous solvent. The gravimetric method of partition coefficient utilizes the miscibility of 1,3-perfluorodimethyl cyclohexane and cyclohexane at elevated temperatures and demixing on cooling to partition the fluorinated material between the two phases. The gravimetric determination method was applied to the fluorinated dendrons (3,4,5) PIVEG1-COOCH₃, (3,4,5-3,4)PPVEG2-COOCH₃, (3,4,5) ²PPVEG2-COOCH₃ possessing 3, 6, and 9 fluorinated groups on their periphery. This method has the advantage that it is simple and economical with respect to the quantity of fluorinated solvent required especially for large molecular mass compounds. The partition coefficient (eq 1) was calculated as the ratio between the masses of fluorinated dendron in the two layers (fluorous versus organic).

$$P=[C_f]/[C_o], \quad (1)$$

where $c_f$ is the concentration of dendron in the fluorous phase and $c_o$ is the concentration of dendron in the organic phase (mol$^{-1}$ dm$^3$). When 100% recovery was obtained in the fluorous phase, the partition coefficient P was denoted at P>100. The dendrons (3,4,5)PPVEG1-COOCH$_3$, (3,4,5-3,4)PPVEG2-COOCH$_3$, and (3,4,5)PPVEG2-COOCH$_3$ showed excellent fluorous phase affinities of P ¼ 18, 49, and >100, respectively, with 95, 98, and 100% recovery of the Dendron in the fluorous phase. Although first generation dendron has, as expected, lower fluorophilicity, second generation (3,4,5)$^2$PPVEG2-COOCH$_3$ showed complete affinity in the fluorous phase.

Disassembly and the Lack of Self-Assembly of PPVE Dendrons

Figure 4A:
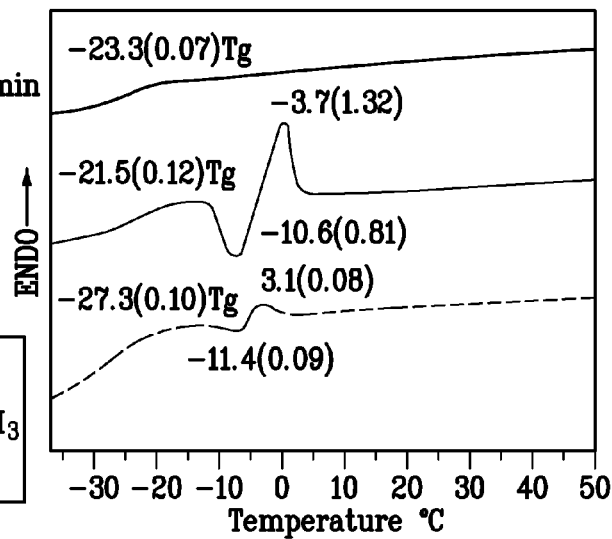
FIG. 4 presents DSC traces (10° C./min) for the PPVE functionalized dendrons (3,4,5)$^2$G2PPVE-COOCH$_3$, (3,4,5-3,4)G2PPVE-COOCH$_3$, and (3,4)$^2$G2PPVE-COOCH$_3$, (a) first heating, (h) second heating, and (c) first cooling scans. The phase transitions and the corresponding enthalpy changes are indicated.
Figure 4B:
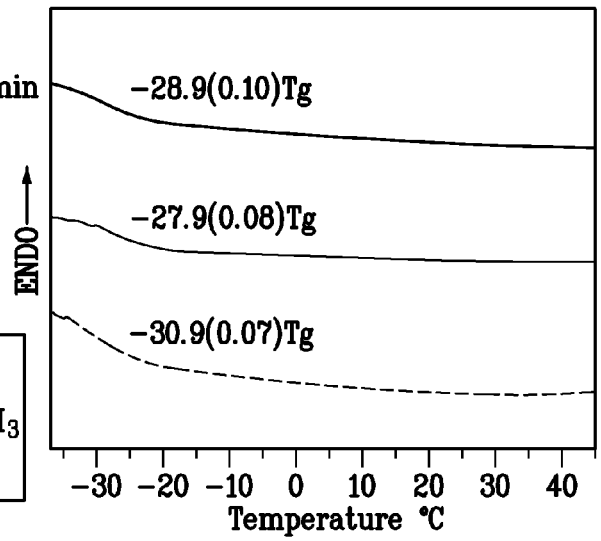
Figure 4C:
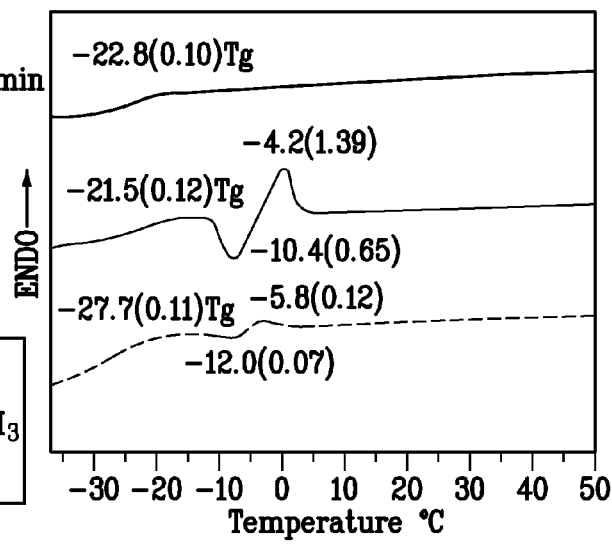

The disassembly and the self-assembly properties of PPVE dendrons were investigated by a combination of differential scanning calorimetry (DSC), thermal optical polarized microscopy (OPM), and by X-ray diffraction (XRD) experiments. Surprisingly, all dendrons are liquids when the parent poly-phenol building blocks are crystalline. Therefore, at room temperature no self-assembly was observed for any of the fluorous dendrons reported. Only glass transitions at low temperatures were observed for compounds (3,4,5)$^2$PPVEG2-COOCH$_3$, (3,4,5-3,4)PPVEG2-COOCH$_3$ and (3,4)$^2$PPVEG2-COOCH$_3$ (FIG. 4) coupled with slow crystallization peaks on heating at −11° C. and −12° C., followed by immediate melting at −4° C. and −6° C., respectively for (3,4,5-3,4)PPVEG2-COOCH$_3$ and (3,4)$^2$PPVE-COOCH$_3$ (FIG. 4). Attempts to characterize the phase formed by (3,4,5-3,4)PPVEG2-COOCH$_3$ and (3,4)$^2$PPVE-COOCH$_3$ by X-ray diffraction experiments were unsuccessful due to overlap of crystallization and melting transitions. In contrast to the semifluorinated benzyl ether dendrons reported previously, where self-assembly into supramolecular columns and spheres at the first and second generation was observed, the new fluorous dendrons reported here mediate only the disassembly process. The term disassembly refers to the dismantling of the original crystalline, liquid crystalline or amorphous state prior to self-assembly into a new supramolecular structure. The lack of self-assembly may be due to the enhanced flexibility of the semifluorinated ether derivative combined with the ability of the acidic —H from the dendron structure to H— bond intramolecularly with the ether oxygen. These results are in line with previous experiments in which semifluorinated ethers were used as spacers in side-chain and main-chain liquid crystalline polymers.

The invention is exemplified by the following examples which are not intended to be limiting.

EXAMPLES

Materials

Aluminum oxide (activated, basic, and neutral Brockmann I, standard grade, 150 mesh, 58 Å) (all from Fisher), silica gel (60 Å, 32-63 lm) (Sorbent Technology), N,N-dimethylformamide (DMF, dry), ethyl acetate, hexane, diethyl ether (all from Fisher, ACS reagents), 3,4-dihydroxybenzoic acid (98%), 3,5-dihydroxybenzoic acid (97%), and 3,4,5-trihydroxybenzoate, potassium tert-butoxide, LiAlH4 (95ƀ%) and perfluorovinylether were used as received. Tetrahydrofuran (Fisher, ACS reagent grade) was refluxed over sodium/benzophenone and freshly distilled before use. Dichloromethane (Fisher, ACS reagent grade) was refluxed over CaH2 and freshly distilled before use. All other chemicals were commercially available and were used as received. Methyl 3,4-dihydroxybenzoate and methyl 3,5-dihydroxybenzoate were prepared from the corresponding acids by esterification with MeOH in the presence of a catalytic amount of H$_2$SO$_4$.

Techniques $^1$H NMR (500 MHz) and $^{13}$C (125 MHz) NMR spectra in solution were recorded on a Bruker DRX 500 instrument using TMS as internal standard and Advance 500 fitted with Bruker Cold (Cryogenic) probe for higher sensitivity $^{13}$C experiments. The purity of the products was determined by a combination of TLC on silica gel coated aluminum plates (with F254 indicator; layer thickness, 200 µm; particle size, 2-25 µm; pore size 60 Å, SIGMA-Aldrich) and high pressure liquid chromatography (HPLC) using THF as mobile phase at 1 mL/min, on a Shimadzu LC-10AT high pressure liquid chromatograph equipped with a Perkin Elmer LC-100 oven (40 C), containing two Perkin Elmer PL gel columns of 5×10$^2$ and 1×10$^4$ Å, a Shimadzu SPD-10A UV detector (λ=254 nm), a Shimadzu RID-10A RI-detector, and a PE Nelson Analytical 900 Series integrator data station. Thermal transitions were determined on a TA Instruments Q100 differential scanning calorimeter (DSC) equipped with a refrigerated cooling system with 10 C min$^{-1}$ heating and cooling rates. Indium was used as calibration standard. The transition temperatures were reported as onset of the maxima and minima of their endothermic and exothermic peaks. Matrix-assisted laser desorption/ionization time-of-flight (MALDI-TOF) mass spectrometry was performed on a PerSeptive Biosystems-Voyager-DE (Framingham, Mass.) mass spectrometer equipped with a nitrogen laser (337 µm) and operating in linear mode. Internal calibration was performed using Angiotensin II and Bombesin as standards. The analytical sample was obtained by mixing the THF solution of the sample (3-15 mg/mL) and THF solution of the matrix [3,5-dihydroxybenzoic acid, 99% (Acros) or 1:1 mixture of 3,5-dihydroxybenzoic acid, 99% (Acros) and silver(I) trifluoroacetate, 98% (Lancaster) dissolved in acetone, 10 mg/mL] in a 1/5 v/v ratio. A total of 0.5 µL of sample-matrix solution was loaded onto the MALDI plate and allowed to dry at rt before the plate was inserted into the vacuum chamber of the MALDI instrument. The laser steps and voltages applied were adjusted depending on both the molecular weight and the nature of each analyzed compound. Several runs from different regions of the sample were collected and the results are presented as accumulated data.

As presented herein, a series of first and second generation AB$_3$ and AB$_2$ benzyl ether dendrons containing short semifluorinated segments on their periphery were synthesized and their fluorous phase behavior was analyzed. The fluorous phase effect is amplified at the same generation by the number of semifluorinated groups and for the same number of semifluorinated groups on the dendron periphery by increasing the generation number. These new fluorous dendrons mediate disassembly of their parent building blocks but do not promote their self-assembly. The disassembly process via fluorous phase is significant for a variety of technological applications.

Synthesis of Fluorous Dendrons

Example 1

(3,4,5)PPVEG1-COOCH$_3$

In a dry two-neck round bottom flask containing methyl 3,4,5-trihydroxybenzoate (5.38 g, 0.03 mol) and potassium tert-butoxide (0.49 g, 8.76 mmol) dissolved in dry DMF (60 mL) was added perfluorovinyl ether (23.32 g, 0.08 mol) under $N_2$. The reaction was stirred at 23° C. for 18 h. The reaction mixture was then poured into ice water containing hydrochloric acid (2 mL) and extracted three times with 100 mL of ether. The organic fractions were combined, washed with water, and dried over magnesium sulphate. The solvent was removed under reduced pressure and the crude product was purified on neutral alumina with hexane:ethyl acetate mixture (7:1) yielding 22.3 g of a clear liquid; (78%). Purity (HPLC), 99+%; $^1$H NMR (500 MHz, $CDCl_3$/Freon113, TMS) d, δ=7.99 (s, 2H, Ar), 6.06 (d, 2J δ=53.5, 3H, —CHF), 3.96 (s, 3H, —CH3). $^{13}$C NMR (126 MHz, $CDCl_3$/HFB, TMS) d δ=163.75, 143.39, 136.58, 130.20, 121.37, 120.42-104.22—$CF_2$—), 98.50-96.56 (—CHF—), 52.78; MALDI-TOF MS calc. for $C_{23}H_8F_{30}O_8+Na^+$: 1004.96. found m/z: 1005.20[M+Na]$^+$.

Example 2

(3,4,5)PPVEG1-CH$_2$OH

A solution of 3,4,5-PPVE-methyl ester (5.3 g, 5.4 mmol) in dry THF (45 mL) was added dropwise under $N_2$ atmosphere to a stirred suspension of $LiAl_4$ (0.3 g, 8.14 mmol) in dry THF (30 mL) cooled to 0° C. in an ice bath. The mixture was stirred at 20° C. for 30 min and the reaction progress was monitored by TLC (ethyl acetate/hexane 1/7 v/v). The excess of hydride was quenched under cooling in an ice bath with $H_2O$ (0.3 mL) followed by NaOH (0.3 mL) and $H_2O$ (1 mL). The organic layer was separated by filtration and the crude compound was passed through a short column of neutral alumina with hexane/ethyl acetate (1/7). Removal of the solvent yielded a clear oil, 4.4 g (85%). Purity (HPLC), 99+%; $^1$H NMR (500 MHz, $CDCl_3$/Freon113, TMS) d, δ=7.35 (s, 2H, Ar), 6.10 (d, 2J δ=44.7, 3H, —CHF), 4.69 (s, 2H, —CH$_2$—); $^{13}$C NMR (126 MHz, $CDCl_3$/HFB, TMS) d, δ=143.37, 142.12, 131.80, 117.74, 120.49-104.30 (—$CF_2$), 98.66-96.72 (—CHF—), 63.27; MALDI-TOF MS calc. for $C_{22}H_8F_{30}O_7+Na^+$: 976.97. found m/z: 976.30 [M+Na]$^+$.

Example 3

(3,4,5)PPVEG1-CH$_2$CL

Into two-neck round bottom flask was added 3,4,5PPVECH$_2$OH (3.72 g, 3.88 mmol) dissolved in 40 mL of dry $CH_2Cl_2$ and 1 drop of dry DMF. The flask was flushed with $N_2$ and cooled to 0° C. in an ice bath. SOCK (0.35 mL, 4.8 mmol) dissolved in 16 mL of dry $CH_2Cl_2$ was added dropwise via a dropping funnel. The reaction was stirred at 23° C. until completion followed by TLC (ethyl acetate/hexane 1/9 v/v) (_30 min). The solvent was removed and the crude oil was redissolved in diethyl ether, washed twice with water and brine and dried over $MgSO_4$. The crude product was passed through a short plug of alumina, concentrated and used without further purification, 3.0 g (80%). Purity (HPLC), $^1$H NMR (500 MHz, $CDCl_3$/Freon113, TMS) d, δ=7.40 (s, 2H, Ar), 6.06 (d, J, δ=53.3, 3H, —CHF), 4.56 (s, 2H, —CH$_2$).

Example 4

(3,4,5-3,4)PPVEG2-COOCH$_3$

A suspension of finely ground dry $K_2CO_3$ (0.7 g, 0.5 mmol) in dry DMF (25 mL) was added to a three-neck round bottom flask equipped with magnetic stirring, heating bath, condenser, and dropping funnel with pressure-equalization arm and degassed at 50° C. for 1 h, under stirring. Methyl 3,4-dihydroxybenzoate (0.14 g, 0.85 mmol) was added, while purging the system with $N_2$. The 3,4,5-PPVE-CH$_2$—Cl (1.65 g, 1.7 mmol) was dissolved in DMF (15 mL) and added to a dropping funnel and flushed with N2 for 30 min. Following the complete dissolution of the phenol in DMF, the chloride was added dropwise to the reaction mixture while the temperature was increased to 60° C. The suspension was stirred at 60° C. under $N_2$ and monitored by TLC. After 4 h the reaction mixture was poured into cold water (1.5 L), stirred for 5 min, and then extracted five times with ethyl acetate (100 mL). The combined organic extracts were washed with water (100 mL), followed by brine (100 mL), and dried over anhydrous $MgSO_4$. Evaporation of the solvent yielded the crude product, which was purified by flash chromatography (basic alumina, hexane/ethyl acetate, 8/1). The pure fractions were collected, and after evaporation resulted in a viscous oil, 1.60 g, 93%. Purity (HPLC), 99+%; $^1$H NMR (500 MHz, $CDCl_3$/Freon113, TMS) d, δ=7.73 (m, 2H, Ar), 7.45 (d, 2J δ=9.1, 3H, Ar), 7.00 (m, Ar), 6.06 (m, 6H, —CHF), 5.18 (m, 4H, —CH2), 3.91 (s, 3H, CH$_3$); $^{13}$C NMR (126 MHz, $CDCl_3$/HFB, TMS) d ¼ 165.41, 152.11, 147.90, 143.76, 143.67, 132.41, 132.32, 124.03, 123.75, 118.51, 118.31, 115.97, 114.89, 120.32-104.06 (—CF$_7$—), 98.72-96.77 (—CHF—), 69.31, 69.14, 52.24; MALDI-TOF MS calc. for $C_{52}H_{20}F_6OO_{16}+Na^+$: 2062.97. found m/z: 2062.67 [M+Na]$^+$.

Example 5

(3,4,5-3,5)PPVEG2-COOCH$_3$

Into a three-neck round bottom flask equipped with magnetic stirring, heating bath, condenser, and dropping funnel with pressure-equalization arm was added a suspension of finely ground dry $K_2CO_3$ (0.76 g, 0.5 mmol) in dry DMF (25 mL) that was subsequently degassed for 1 h, under stirring. Methyl 3,5-dihydroxybenzoate (0.15 g, 0.91 mmol) was added, while purging the system with $N_2$. The 3,4,5-PPVECH$_2$—Cl (1.75 g, 1.83 mmol) was dissolved in DMF (15 mL) and added to a dropping funnel and flushed with $N_2$ for 30 min. After the complete dissolution of the phenol in DMF, the chloride was added dropwise to the reaction mixture and the temperature was increased to 60° C. The suspension was stirred at 60° C. under $N_2$ and monitored by TLC. After 4 h the reaction mixture was poured into ice-cold water (15 mL), stirred for 5 min and then extracted five times with ethyl acetate (100 mL). The combined organic extracts were washed with water (100 mL), brine (100 mL), and dried on anhydrous $MgSO_4$. Evaporation of the solvent yielded the crude product, which was purified by flash chromatography (basic alumina, hexane/ethyl acetate, 8/1). The pure fractions were collected, and after evaporation resulted in a viscous oil, 1.2 g, 65%. Purity (HPLC), 99+%; $^1$H NMR (500 MHz, $CDCl_3$/Freon113, TMS) d, δ=7.64 (s, 4H, Ar), 7.26 (s, 2H, Ar, 6.91 (m, 1H, Ar), 6.20 (m, 6H, —CHF), 5.24 (s, 4H, —CH$_2$), 3.99 (s, 3H, —CH$_3$); $^{13}$C NMR (126 MHz, $CDCl_3$/HFB, TMS) d, δ=161.98, 159.23, 143.61, 132.57, 132.43, 132.38, 120.51-104.33 (—$CF_2$), 98.69-96.75 (—CHF), 118.70, 107.87, 106.40; MALDI-TOF MS calc. for $C_{52}H_{20}F_{60}O_{16}+Na^+$: 2062.97. found m/z: 2062.54 [M+Na]$^+$.

Example 6

(3,4,5)$^2$PPVEG2-COOCH$_3$

A suspension of finely ground dry $K_2CO_3$ (1.5 g, 0.01 mol) in dry DMF (50 mL) was added to a three-neck round bottom flask equipped with magnetic stirring, heating bath, condenser, and dropping funnel with pressure-equalization arm and degassed at 50° C. for 1 h, under stirring. Methyl 3,4,5-trihydroxybenzoate (0.22 g, 1.23 mmol) was added, while purging the system with $N_2$. The 3,4,5-PPVE-CH2-Cl (3.22 g, 1.23 mmol) was dissolved in DMF (20 mL) and added to a dropping funnel and flushed with $N_2$ for 30 min. Following the complete dissolution of the phenol in DMF, the chloride was added dropwise to the reaction mixture while the temperature was increased to 60° C. The suspension was stirred at 60° C. under N2 and monitored by TLC. After 4 h the reaction mixture was poured into ice-cold water (20 mL), and stirred for 5 rain, and then extracted five times with ethyl acetate (100 mL). The combined organic extracts were washed with water (100 mL), brine (100 mL), and dried on anhydrous $MgSO_4$. Evaporation of the solvent yielded the crude product, which was purified by flash chromatography (basic alumina, hexane/ethyl acetate, 8/1). The pure fractions were collected, and after evaporation resulted in a viscous oil, 2.5 g, 70%. Purity (HPLC), 99+%; NMR (500 MHz, Freon113/$CDCl_3$, TMS) d, δ=7.43 (s, 6H, Ar), 7.23 (s, 2H, Ar), 6.0 (m, CHF), 5.16 (s, 6H, —$CH_2$—), 3.90 (s, 3H, —$CH_3$); $^{13}C$ NMR (126 MHz, $CDCl_3$/HFB, TMS) d, δ=165.46, 151.72, 143.77, 143.40, 141.40, 132.44, 126.20, 120.50-104.33 (—$CF_2$), 118.29, 108.71, 98.66-96.72 (—CHF), 69.29, 51.41; MALDI-TOF MS calc. for $C_{52}H_{20}F_{60}O_{16}$+Ag+: 3098.85. found m/z: 3099.20 $[M+Na]^+$.

Example 7

(3,4)PPVEG1-$COOCH_3$

Into a dried two-neck round bottom flask containing methyl 3,4-dihydroxybenzoate (2 g, 0.01 mol) and potassium tertbutoxide (0.2 g 1.0 mmol) dissolved in dry DMF (20 mL) was added perfluorovinyl ether (6.33 g, 0.02 mol) under $N_2$ and left stirring at 23° C. for 18 h. The reaction mixture was then poured into ice water containing hydrochloric acid (2 mL), and extracted three times with ether (100 mL), and washed with water and dried over $MgSO_4$. The solvent was removed under reduced pressure and the crude product was purified on neutral alumina with hexane:ethyl acetate mixture (7:1) yielding a colorless liquid; 7.5 g (90%). Purity (HPLC), 99+%; NMR (500 MHz, $CDCl_3$/Freon113, TMS) d, δ=8.03 (m, 2H, Ar), 7.47 (d, 2J δ=8.6, 1H, Ar), 6.09 (d, 2J δ=53.6, 2H, —CHF), 3.81 (s, 3H, —$CH_3$); $^{13}C$ NMR (126 MHz, $CDCl_3$/HFB, TMS) d, δ=164.67, 144.58, 140.37, 129.39, 128.54, 124.77, 122.45, 120.40-104.25 (—$CF_2$), 98.67-96.69 (—CHF), 51.99; MALDI-TOF MS calc. for $C_{18}H_8F_{20}O_6$+Ag+: 722.99. found m/z: 723.45 $[M+Na]^+$ Example 8

(3,4)PPVEG1-$CH_2OH$

A solution of 3,4-PPVE-methyl ester (3.16 g, 4.5 mmol) in dry THF (15 mL) was added dropwise under N atmosphere to a stirred suspension of $LiAlH_4$ (0.25 g, 6.76 mmol) in dry THF (10 mL) cooled to 0° C. in an ice bath. The mixture was stirred at 20° C. for 30 min when the reaction was shown to be completed by TLC (ethyl acetate/hexane 1/7 v/v). The excess of hydride was quenched under cooling on ice bath with 0.3 mL $H_2O$ followed by 0.3 ml. NaOH and 1 mL of $H_2O$. The organic layer was separated by filtration and the crude compound was passed through a short column of neutral alumina with hexane/ethyl acetate (1/7). Removal of the solvent resulted in a clear oil, 2.66 g (88%). Purity (HPLC), 99+%; $^1H$ NMR (500 MHz, $CDCl_3$/Freon113, TMS): d, δ=7.40 (s, 1H, Ar), 7.35 (d, 2J δ=8.6, 1H, Ar), 7.30 (d, 2J δ=9.0, 0H, 1H, Ar), 6.06 (d, 2J δ=53.8, 1H, —CHF), 4.73 (s, —$CH_2$); MALDI-TOF MS calc. for $C_{17}H_8F_{20}O_{5+}Ag^+$: 649.99. found m/z: 650.12 $[M+Na]^+$.

Example 9

(3,4)PPVEG1-$CH_2Cl$

Into a two-neck round bottom flask was added 3,4 $PPVECH_2OH$ (2.55 g, 3.8 mmol) dissolved in dry $CH_2Cl_2$ (45 mL) and 1 drop of dry DMF. The flask was flushed with $N_2$ and cooled to 0° C. in an ice bath. SOCl2 (0.35 mL, 4.74 mmol) dissolved in dry $CH_2Cl_2$ (5 mL) was added dropwise via a dropping funnel. The reaction was left stirring at 23° C. until completion followed by TLC (ethyl acetate/hexane 1/8 v/v) (~1 h). The solvent was removed and the crude oil was redissolved in diethyl ether, washed twice with water and brine and dried over $MgSO_4$. The crude product was passed quickly through a short plug of alumina concentrated and used immediately in the next step, 2.5 g (95%).

Example 10

(3,4)$^2$PPVEG2-$COOCH_3$

In a three-neck round bottom flask equipped with magnetic stirring, heating bath, condenser, and dropping funnel with pressure-equalization arm was added a suspension of finely ground dry $K_2CO_3$ (1.57 g, 0.01 mol) in dry DMF (35 mL) that was subsequently degassed at 50° C. for 1 h, under stirring. Methyl 3,4-dihydroxybenzoate (0, 32 g, 1.89 mmol) was added, while purging the system with $N_2$. The 3,4-PPVE-$CH_2$—Cl (2.62 g, 3.79 mmol) was dissolved in DMF (35 mL) and added to a dropping funnel while flushed with $N_2$ for 30 min. After the complete dissolution of the phenol in DMF, the chloride was added through the dropping funnel to the reaction mixture while the temperature was increased to 60° C. The suspension was stirred at 60° C. under $N_2$ and monitored by TLC. After 5 h the reaction mixture was poured into ice-cold water (0.5 L), stirred for 5 min, and then extracted five times with ethyl acetate (100 mL). The combined organic extracts were washed with water (100 mL), brine (100 mL), and dried on anhydrous $MgSO^4$. Evaporation of the solvent yielded the crude product, which was purified by flash chromatography (basic alumina, hexane/ethyl acetate, 8/1). The pure fractions were collected, and after the evaporation of the solvent resulted in a viscous oil, 2.40 g, (87%). Purity (HPLC), 99+%; 1H NMR (500 MHz, $CDCl_3$/Freon113, TMS): d, δ=7.70-7.62 (m, 6H, Ar), 7.53 (s, 1H, Ar), 7.43 (m, 1H, Ar), 6.20 (d, 2J δ=53.8, 1H, ACHF), 5.37 (s, 2H, —$CH_2$—O), 5.31 (s, 2H, $CH_2$—O), 3.96 (s, 3H, —$CH_3$); $^{13}C$ NMR (126 MHz, $CDCl_1$/HFB) d 165.75, 152.31, 148.03, 140.98, 140.94, 140.39, 140.30, 125.36, 123.59, 121.74, 115.98, 114.49, 112.46, 120.52-104.36 (—$CHF_2$), 98.65-98.62 (—CHF), 69.41, 69.24, 50.83; MALDI-TOF MS calc. for $C_{42}H_{20}F_{40}O_{12}$+$Na^+$: 1499.53. found m/z: 1497.75 $[M+Na]^+$.

Example 11

Gravimetric Determination of Partition Coefficients

A known quantity of fluorinated dendron was dissolved in 1.1 homogeneous mixture obtained at 60° C. of 1,3-perfluorodimethyl cyclohexane:cyclohexane. The solution was allowed to cool slowly to room temperature when the two solvents become immiscible. The solutions were allowed to sit in a sealed flask at 25° C. for 12 h prior to separation to allow the solution to reach an equilibrium state. The partition coefficient was obtained as the ratio between the mass determined gravimetrically of fluorinated dendron in the two layers. The results are averaged over three experiments.

$$P=[c]_f/[c]_o; P=[m(g)]_f/[m)g)]_o;$$

f=fluorous phase; o=organic phase:

Typical Procedure

Into a 25-mL conical separating flask was measured 1.09 g of dendron and added 20 mL of hot 1:1 mixture of PFCy:Cy. The flask was sealed and allowed to stand at 25° C. for 12 h. The phases were separated and the partition coefficient was determined gravimetrically by determining the amount of dendron in each organic and fluorous phase.

What is claimed:

1. A method of producing a fluorous dendron comprising reacting a compound of formula II

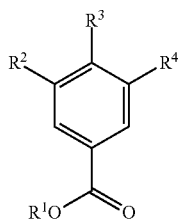

with a compound of formula III

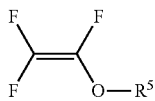

to produce a compound of the formula I

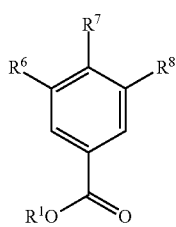

wherein:

$R^1$ is a $C_1$-$C_6$ alkyl group;

each of $R^2$-$R^4$ is, independently, H or OH; provided at least two of $R^2$-$R^4$ are OH;

$R^5$ is a $C_1$-$C_9$ perfluoroalkyl group, said $C_1$-$C_9$ perfluoroalkyl group optionally containing 1 or 2 ether oxygens; and each of $R^6$-$R^8$ is, independently, H or a group of the formula

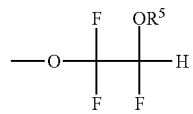

provided that at least two of $R^6$-$R^8$ are a group of the formula

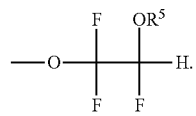

2. The method of claim 1, wherein $R^1$ is methyl.

3. The method of claim 1, wherein $R^5$ is a perfluoropropyl group.

4. The method of claim 1, wherein said perfluoropropyl group is perfluoro-n-propyl.

5. The method of claim 1, further comprising reacting the compound of formula I with a reducing agent to produce a compound of formula IV

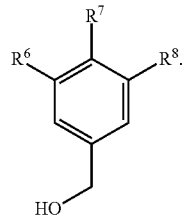

6. The method of claim 5, wherein said reducing agent is LiAlH$_4$.

7. The method of claim 5, further comprising reacting the compound of formula IV with a chlorinating agent to produce a compound of formula V

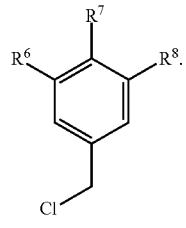

8. The method of claim 7, wherein said chlorinating agent is SOCl$_2$.

9. The method of claim 7, further comprising reacting a compound of formula V with a compound of formula VI

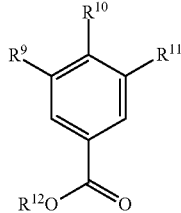

VI to produce a compound of formula VII

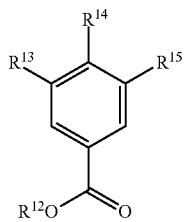

VII wherein:

$R^{12}$ is a $C_1$-$C_6$ alkyl group;

each of $R^9$, $R^{10}$ and $R^{11}$ is independently H or OH; provided that at least two of $R^9$, $R^{10}$ and $R^{11}$ are OH;

each of $R^{13}$, $R^{14}$ and $R^{15}$ is independently H or a group of the formula VIII

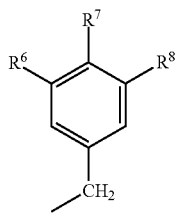

VIII provided that at least two of $R^{13}$, $R^{14}$ and $R^{15}$ are of formula VIII.

10. A compound of the formula

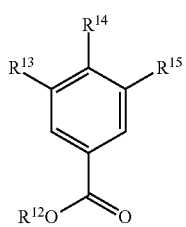

VII wherein:

$R^{12}$ is a $C_1$-$C_6$ alkyl group;

each of $R^{13}$, $R^{14}$ and $R^{15}$ is independently H or a group of the formula VIII

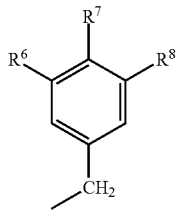

VIII provided that at least two of $R^{13}$, $R^{14}$ and $R^{15}$ are of formula VIII;

each of $R^6$-$R^8$ is, independently, H or a group of the formula

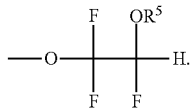

provided that at least two of $R^6$-$R^8$ are a group of the formula

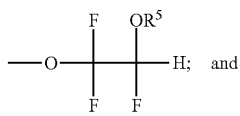 and $R^5$ is a $C_1$-$C_9$ perfluoroalkyl group, said $C_1$-$C_9$ perfluoroalkyl group optionally containing 1 or 2 ether oxygens.

11. The compound of claim 10, wherein $R^{12}$ is methyl.

12. The compound of claim 10, wherein $R^5$ is a perfluoropropyl group.

13. The compound of claim 12, wherein said perfluoropropyl group is perfluoro-n-propyl.

14. A compound of the formula

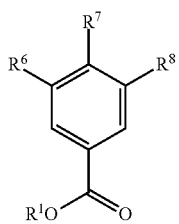

I wherein:

$R^1$ is a $C_1$-$C_6$ alkyl group;

$R^5$ is a $C_1$-$C_9$ perfluoroalkyl group, said $C_1$-$C_9$ perfluoroalkyl group optionally containing 1 or 2 ether oxygens; and each of $R^6$-$R^8$ is, independently, H or a group of the formula
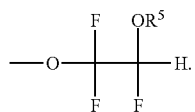
provided that at least two of $R^6$-$R^8$ are a group of the formula
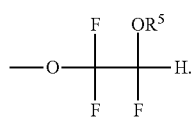
15. The compound of claim 14, wherein $R^1$ is methyl.
16. The compound of claim 15, wherein $R^5$ is a perfluoropropyl group.
17. The compound of claim 16, wherein said perfluoropropyl group is perfluoro-n-propyl.
* * * * *